United States Patent

Laas et al.

[11] 4,240,963
[45] Dec. 23, 1980

[54] PREPARATION OF INDOLENINES

[75] Inventors: Harald Laas, Maxdorf; Axel Nissen, Leimen; Hans-Joachim Opgenorth, Frankenthal; Horst Scheuermann, Ludwigshafen; Hans-Richard Mueller, Bobenheim-Roxheim; Wolfgang Schulte, Hassloch, all of Fed. Rep. of Germany

[73] Assignee: BASF Aktiengesellschaft, Ludwigshafen, Fed. Rep. of Germany

[21] Appl. No.: 64,981

[22] Filed: Aug. 9, 1979

[30] Foreign Application Priority Data

Aug. 7, 1978 [DE] Fed. Rep. of Germany ....... 2834607

[51] Int. Cl.³ .................. C07D 209/08; C07D 263/22
[52] U.S. Cl. ................................. 260/319.1; 548/216; 548/229
[58] Field of Search ............................. 548/216, 229; 260/319.1

[56] References Cited

FOREIGN PATENT DOCUMENTS 2304589  8/1974 Fed. Rep. of Germany ........... 548/229
2514759 10/1975 Fed. Rep. of Germany .
2003139  3/1979 United Kingdom .................. 260/319.1

Primary Examiner—Donald G. Daus
Assistant Examiner—M. C. Eakin
Attorney, Agent, or Firm—Oblon, Fisher, Spivak, McClelland & Maier

[57] ABSTRACT

A process for the preparation of an indolenine of the general formula I

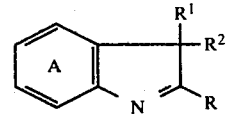

where R, $R^1$ and $R^2$ are aliphatic radicals and $R^1$ and $R^2$ may also be linked and the ring A may be additionally substituted, wherein a compound of the formula II

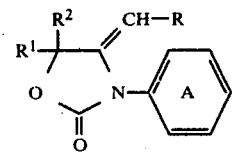

is heated in the presence of a Lewis acid and of a halide.

The products are valuable starting compounds for the preparation of dyes.

9 Claims, No Drawings

PREPARATION OF INDOLENINES

The present invention relates to a process for the preparation of a compound of the general formula I

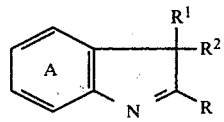

where R, $R^1$ and $R^2$ are aliphatic radicals and $R^1$ and $R^2$ may also be linked and the ring A may be additionally substituted, wherein a compound of the formula II

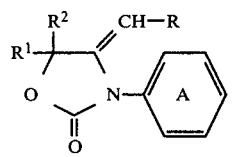

is heated in the presence of a Lewis acid and of a halide. Examples of aliphatic radicals R, $R^1$ and $R^2$ are $C_1$–$C_9$-alkyl or -alkenyl, more specifically ethyl, propyl, butyl, hexyl, octyl, nonyl and allyl, and especially methyl.

Examples of suitable substituents of the ring A are chlorine, bromine, nitro, cyano, $C_1$–$C_4$-alkoxycarbonyl, eg. methoxycarbonyl, ethoxycarbonyl or butoxycarbonyl, alkylsulfonyl, eg. methylsulfonyl or ethylsulfonyl, alkyl, eg. methyl, ethyl, propyl or butyl, and alkoxy, eg. methoxy or ethoxy. The ring A may also carry a fused benzene ring.

Examples of suitable Lewis acids for the reaction are tin-II chloride, tin-IV chloride, titanium tetrachloride, boron trifluoride, aluminum chloride, iron-III chloride and especially zinc chloride. The reaction apparently requires the presence of a halide; other examples of suitable halide additives are NaCl, KCl, LiCl, $MgCl_2$, $CaCl_2$, $BaCl_2$, NaBr, NaI, LiI and KI. The use of a halogen-containing Lewis acid, especially of zinc chloride, is preferred. A combination of, for example, a zinc salt not containing halogen, and a halide, can at times also be advantageous. The combination of zinc chloride and lithium chloride in a molar ratio of from about 1:0.5 to 1:4, preferably 1:2, is particularly preferred.

The process according to the invention is advantageously carried out by heating a compound of the formula II, in the presence or absence of a solvent, with the Lewis acid and the halide at from 150° to 250° C., preferably from 180° to 220° C. The reaction to give the compound of the formula I takes place with elimination of $CO_2$ and is as a rule complete after from 2 to 20 hours.

Per mole of compound II, it is advantageous to use from 1 to 50 mole percent, preferably from 5 to 15 mole percent, of Lewis acid plus halide, if any.

Suitable solvents for the reaction are, in particular, high-boiling compounds which are inert under the reaction conditions: examples are silicone oils and, preferably, mineral oils, which can of course be recycled, together with the catalyst, after isolating the reaction product.

A compound of the formula II is obtained from a compound of the formula III

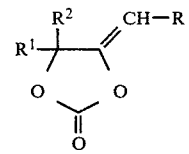

by reaction with an amine of the formula IV

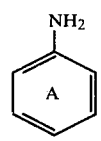

at an elevated temperature, with removal of water. The amine of the formula IV is advantageously employed in excess, a molar ratio of from 1:1.5 to 1:3 being preferred.

In a particularly preferred variant of the process according to the invention, the latter is preceded by the preparation of the compound of the formula II, and this compound is converted, without isolation, to a compound of the formula I in a one-vessel process.

The process according to the invention is of particular importance for the preparation of a compound of the formula Ia

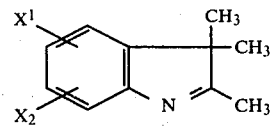

where $X^1$ is hydrogen, chlorine, methyl or methoxy and $X^2$ is hydrogen, chlorine or methyl.

In the Examples which follow, parts and percentages are by weight, unless stated otherwise.

EXAMPLE 1

A mixture of 1,024 parts of 4,4-dimethyl-3-methylene-dioxolanone and 372 parts of aniline is added dropwise over 6 hours to a mixture, boiling under reflux, of 1,116 parts of aniline, 400 parts of mineral oil and 80 parts of zinc chloride, whilst stirring. Simultaneously with the evolution of $CO_2$, water is eliminated and distils continuously from the reaction mixture. After completion of the dropwise addition, the mixture is stirred for a further 10 hours at 210° C. On subsequent distillation, 992 parts of 2-methyl-3,3-dimethyl-indolenine (78% of theory) are obtained.

EXAMPLE 2

A mixture of 128 parts of 4,4-dimethyl-3-methylene-dioxolanone 112 parts of aniline, 100 parts of o-xylene and 5 parts of zinc chloride is heated under a water separator. 18 parts of water are removed in 12 hours. 198 parts of 1-phenyl-4,4-dimethyl-5-methylene-oxazolidinone (97.6% of theory) are isolated. Melting point 115°–116° C.

EXAMPLE 3

203 parts of 1-phenyl-4,4-dimethyl-5-methylene-oxazolidinone are thoroughly mixed with 20 parts of $ZnCl_2$ and then heated to 210° C. Elimination of $CO_2$ is complete after 8 hours. 97 parts of indolenine (61.6% of theory) are isolated.

EXAMPLE 4

203 parts of 1-phenyl-4,4-dimethyl-4-methylene-oxazolidinone and 20 parts of $ZnCl_2$ are jointly suspended in 100 parts of a high-boiling mineral oil and then heated for 8 hours at 210° C. On subsequent distillation, 113 parts of indolenine (71.2%) are obtained.

The following oxazolidinone derivatives can be prepared by a method similar to Example 2:

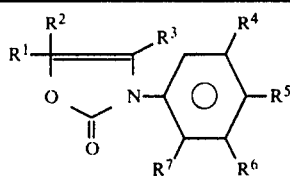

| Example | $R_1$ | $R_2$ | $R_3$ | $R_4$ | $R_5$ | $R_6$ | $R_7$ | Yield | Melting point °C. |
|---|---|---|---|---|---|---|---|---|---|
| 5 | $CH_3$ | $C_2H_5$ | H | H | H | H | H | 47.4% | 131-132 |
| 6 | $CH_3$ | $CH_3$ | H | Cl | Cl | H | H | 38.7% | 118-119 |
| 7 | $CH_3$ | $CH_3$ | H | H | Cl | H | H | 40.3% | 114-117 |
| 8 | $CH_3$ | $CH_3$ | fused benzene ring | H | | H | H | 28.3% | 112 |
| 9 | $CH_3$ | $CH_3$ | H | H | $OC_2H_5$ | H | H | 47.2% | 68 |
| 10 | $CH_3$ | $CH_3$ | H | H | $CH_3$ | H | H | 45.3% | 205 |
| 11 | cyclohexyl | H | H | H | H | H | H | 74.2% | 148-150 |
| 12 | $CH_3$ | $CH_3$ | H | H | $Cl_2C_2H_5$ | H | H | 35.3% | 91-93 |

The oxazolidinone derivatives listed under Examples 5-12 can be converted to the corresponding indolenine derivatives by the method described in Example 1, 3 or 4.

The compounds of Examples 13 to 19 were prepared by methods similar to that of Example 4.

| Example | $R_1$ | $R_2$ | $R_3$ | $R_4$ | $R_5$ | $R_6$ | Yield | Boiling point °C. |
|---|---|---|---|---|---|---|---|---|
| 13 | $CH_3$ | $C_2H_5$ | H | H | H | H | 29.5% | 112-124/2 |
| 14 | $CH_3$ | $CH_3$ | H | Cl | Cl | H | 42.3% | 122-113/1 |
| 15 | $CH_3$ | $CH_3$ | H | H | Cl | H | 29.7% | 80-82/0.3 |
| 16 | $CH_3$ | $CH_3$ | fused benzene ring | H | | H | 39.3% | 125/0.5 |
| 17 | $CH_3$ | $CH_3$ | H | H | $OC_2H_5$ | H | 50.7% | 110-112/1.5 |
| 18 | $CH_3$ | $CH_3$ | H | H | $CH_3$ | H | 11.6% | 77-78/1 |
| 19 | $CH_3$ | $CH_3$ | H | H | $CO_2C_2H_5$ | H | 15.3% | 102-104/1.5 |

EXAMPLE 20

A mixture of 1,024 parts of 4,4-dimethyl-3-methylene-dioxolanone and 372 parts of aniline is added, over 6 hours, to a mixture, boiling under reflux, of 1,116 parts of aniline, 400 parts of mineral oil, 80 parts of zinc chloride and 55 parts of lithium chloride. Simultaneously with the evolution of $CO_2$, water is eliminated; this distils from the reaction mixture together with the aniline and, after cooling, is separated from the aniline, using a continuous water separator. The aniline is returned to the reaction mixture. After completion of the feed, the mixture is stirred for a further 10 hours at 205°-210° C. to complete the reaction. On subsequent distillation, 1,102 parts of 2-methyl-3,3-dimethyl-indolenine (86.6% of theory) are obtained.

We claim:

1. A process for the preparation of an indolenine of the formula:

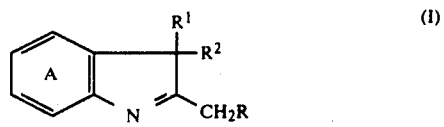

wherein R, $R^1$ and $R^2$ are $C_1$-$C_9$ alkyl or $C_1$-$C_9$ alkenyl and $R^1$ and $R^2$ may also be linked and ring A is optionally substituted with at least one substituent selected from the group consisting of chlorine, bromine, nitro, cyano, $C_1$-$C_4$ alkoxycarbonyl, alkylsulfonyl, alkyl and alkoxy or a fused benzene ring may be attached to said A ring, comprising:

heating a compound of the formula:

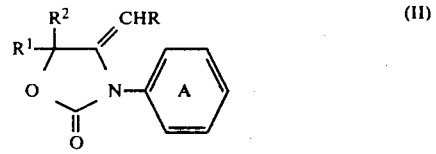

in the presence of a Lewis acid and an alkali metal halide or alkaline earth metal halide.

2. A process for the preparation of an indolenine of the formula:

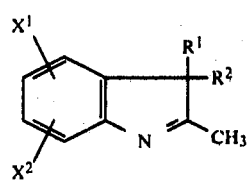

wherein

R$^1$ and R$^2$ are C$_1$ to C$_4$ alkyl, X$^1$ is hydrogen, chlorine, methyl or methoxy and X$^2$ is hydrogen, chlorine or methyl, comprising: heating a compound of the formula:

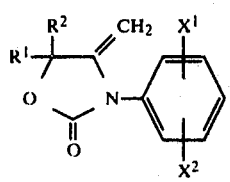

in the presence of a Lewis acid and an alkali metal halide or alkaline earth metal halide.

3. The process as claimed in claim 2, wherein said indolenine compound has the formula:

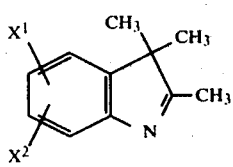

where X$^1$ is hydrogen, chlorine, methyl or methoxy and X$^2$ is hydrogen, chlorine or methyl.

4. The process as claimed in claim 2, wherein said Lewis acid is zinc chloride and said alkali metal halide is lithium chloride.

5. The process as claimed in claim 1, wherein said compound of formula II is prepared by reacting a compound of the formula:

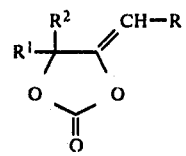

with a compound of the formula:

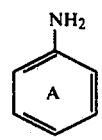

and is then reacted further, without isolation, as set forth in claim 5 to give said indolenine compound.

6. The process as claimed in claim 1, wherein said compound of formula II is heated at a temperature of 150° C. to 250° C.

7. The process as claimed in claim 1, wherein the heating of said compound of formula (II) is conducted in the presence of a solvent selected from the group consisting of silicon oils and mineral oils.

8. The process as claimed in claim 1, wherein said Lewis acid is tin (II) chloride, tin (IV) chloride, titanium tetrachloride, boron trifluoride, aluminum chloride, iron (III) chloride or zinc chloride, and wherein said alkali metal halide is NaCl, KCl, LiCl, NaBr, NaI, LiI or KI and said alkaline earth metal halide is MgCl, BaCl$_2$ or CaCl$_2$.

9. The process ad claimed in claim 1, wherein from 1 to 50 mole percent of said Lewis acid and alkali metal halide or a alkaline earth metal halide is reacted with one mole of said compound II.

* * * * *